United States Patent
Kelly

(10) Patent No.: US 11,224,589 B2
(45) Date of Patent: Jan. 18, 2022

(54) COMPOSITIONS FOR A DIETARY SUPPLEMENT TO IMPROVE SLEEP

(71) Applicant: Neurohacker Collective LLC, Carlsbad, CA (US)

(72) Inventor: Gregory Kelly, San Diego, CA (US)

(73) Assignee: Neurohacker Collective, LLC, Carlsbad, CA (US)

( * ) Notice: Subject to any disclaimer, the term of this patent is extended or adjusted under 35 U.S.C. 154(b) by 0 days.

(21) Appl. No.: 16/833,117

(22) Filed: Mar. 27, 2020

(65) Prior Publication Data

US 2021/0299097 A1    Sep. 30, 2021

(51) Int. Cl.

| | | |
|---|---|---|
| *A61K 36/00* | (2006.01) | |
| *A61K 31/405* | (2006.01) | |
| *A61K 31/198* | (2006.01) | |
| *A61K 36/074* | (2006.01) | |
| *A61K 31/7072* | (2006.01) | |
| *A61K 31/05* | (2006.01) | |
| *A61K 9/00* | (2006.01) | |
| *A61K 45/06* | (2006.01) | |
| *A61K 31/122* | (2006.01) | |
| *A61K 31/01* | (2006.01) | |
| *A61K 36/734* | (2006.01) | |
| *A61K 31/7048* | (2006.01) | |

(52) U.S. Cl.
CPC .......... *A61K 31/405* (2013.01); *A61K 9/0053* (2013.01); *A61K 31/01* (2013.01); *A61K 31/05* (2013.01); *A61K 31/122* (2013.01); *A61K 31/198* (2013.01); *A61K 31/7048* (2013.01); *A61K 31/7072* (2013.01); *A61K 36/074* (2013.01); *A61K 36/734* (2013.01); *A61K 45/06* (2013.01)

(58) Field of Classification Search
CPC .................................................. A61B 5/4815
See application file for complete search history.

(56) References Cited

U.S. PATENT DOCUMENTS

2006/0275520 A1 * 12/2006 Ikonte .................... A61K 36/65
424/773

FOREIGN PATENT DOCUMENTS

JP          60136515 A  *  7/1985
WO     WO-2019005962 A1  *  1/2019  ............. A61K 45/06

* cited by examiner

*Primary Examiner* — Qiuwen Mi
(74) *Attorney, Agent, or Firm* — Insigne PC

(57) ABSTRACT

A composition for improving sleep. In one embodiment, the composition comprises L-Tryptophan, L-Theanine, Reishi mushroom extract, Uridine, a polyphenol, and paeoniflorin. In certain embodiments, the composition further comprises citrus bioflavonoid extract, γ-Oryzanol, holy basil extract, saffron extract, *Schisandra chinensis* extract, sesamin extract, blueberry extract, quercetin, *Polygala tenuifolia* root extract, gotu kola extract, ashwagandha extract, betaine, magnesium, or combinations thereof. In other embodiments, the composition further comprises astaxanthin, lycopene, hawthorne extract, or combinations thereof. In certain embodiments, the composition is incorporated into pills. A method for promoting the brain pathways involved in sleep, relaxation, and calmness comprising: ingesting a composition comprising L-Tryptophan, L-Theanine, Reishi mushroom extract, Uridine, a polyphenol, and paeoniflorin. In one method, the composition is ingested at least one and a half hours before bedtime.

5 Claims, 3 Drawing Sheets

| Ingredient | Exemplary Amounts (mg) |
|---|---|
| L-Tryptophan | 100-250 |
| L-Theanine | 50-100 |
| Reishi mushroom extract (*Ganoderma lingzhi*) | 400-600 |
| Uridine | 25-100 |
| Grape and/or Olive polyphenols (fruit, vine, seed) | 30-100 |
| Paeoniflorin (from White Peony Root extract) | 2-10 |

FIG. 1

| Ingredient | Exemplary Amounts (mg) |
|---|---|
| L-Tryptophan | 100-250 |
| L-Theanine | 50-100 |
| Reishi mushroom extract (*Ganoderma lingzhi*) | 400-600 |
| Uridine | 25-100 |
| Grape and/or Olive polyphenols (fruit, vine, seed) | 30-100 |
| Paeoniflorin (from White Peony Root extract) | 2-10 |
| Citrus Bioflavonoid extract | 25-75 |
| γ-Oryzanol (from Rice Bran Extract) | 20-50 |
| Holy Basil extract (*Ocimum sanctum*) | 150-400 |
| Saffron (*Crocus sativa*) extract | 10-20 |
| *Schisandra chinensis* extract | 100-200 |
| Sesamin (from Sesame extract) | 5-10 |
| Blueberry Extract | 75-125 |
| Quercetin | 2-10 |
| *Polygala tenuifolia* Root extract | 50-150 |
| *Zizyphus jujuba* extract | 100-200 |
| Gotu Kola extract (*Centella asiatica*) | 100-200 |
| Ashwagandha extract (*Withania somnifera*) | 100-200 |
| Betaine (trimethylglycine) | 50-150 |
| Magnesium | 25-100 |
| Vitamin B6 | 1-2 |

FIG. 2

| Ingredient | Exemplary Amounts (mg) |
|---|---|
| L-Tryptophan | 100-250 |
| L-Theanine | 50-100 |
| Reishi mushroom extract (*Ganoderma lingzhi*) | 400-600 |
| Uridine | 25-100 |
| Grape and/or Olive polyphenols (fruit, vine, seed) | 30-100 |
| Paeoniflorin (from White Paeony Root extract) | 2-10 |
| Citrus Bioflavonoid extract | 25-75 |
| γ-Oryzanol (from Rice Bran Extract) | 20-50 |
| Holy Basil extract (*Ocimum sanctum*) | 150-400 |
| Saffron (*Crocus sativa*) extract | 10-20 |
| *Schisandra chinensis* extract | 100-200 |
| Sesamin (from Sesame extract) | 5-10 |
| Blueberry Extract | 75-125 |
| Quercetin | 2-10 |
| *Polygala tenuifolia* Root extract | 50-150 |
| *Zizyphus jujuba* extract | 100-200 |
| Gotu Kola extract (*Centella asiatica*) | 100-200 |
| Ashwagandha extract (*Withania somnifera*) | 100-200 |
| Betaine (trimethylglycine) | 50-150 |
| Magnesium | 25-100 |
| Vitamin B6 | 1-2 |
| Astaxanthin | 2-5 |
| Lycopene | 3-10 |
| Hawthorn extract (*Crataegus sp*) | 100-200 |

FIG. 3

COMPOSITIONS FOR A DIETARY SUPPLEMENT TO IMPROVE SLEEP

BACKGROUND OF THE INVENTION

1. Field of Invention

The present invention relates to dietary supplements to improve sleep, relaxation, and calmness.

2. Description of Related Art

Sleep is a natural brain state that is characterized by altered consciousness that differs from wakefulness by a decreased ability to react to stimuli. Most creatures within the animal kingdom experience some version of sleep. Although the exact biological purpose of sleep is unknown, sleep is essential to everyday health and wellbeing. Sleep plays a critical role in the brain's ability to form new memories. Studies have shown that not getting enough sleep increases the risk of cardiovascular disorders, stroke, high blood pressure, diabetes, depression, and obesity. Sleep deprivation can also decrease the body's immunity and make fighting off common infections harder. The Center for Disease Control estimates that more than a third of American adults do not get enough sleep, defined as at least seven hours per day.

Sleep is characterized into different brain states that include rapid eye movement (REM) sleep, in which brain activity becomes more rhythmic and similar to brain activity during wakefulness, and non-REM sleep, in which brain activity becomes slower and irregular. It has been thought of that sleep is regulated by two biological mechanisms: circadian rhythms and sleep-wake homeostasis. Circadian rhythms control a variety of bodily functions throughout the day including wakefulness and metabolism. Circadian rhythms are often disrupted in the case of jet lag due to a mismatch between the body's biological clock and external clock. Circadian rhythms are controlled by the body's biological clock that is approximately 24 hours and is synchronized with environmental cues including sunlight. Sleep-wake homeostasis is another biological mechanism that controls the wake-sleep cycle. It is thought that this homeostasis reminds the body to sleep after a period of deprivation and that this drive gets stronger the longer you are awake.

Various forms of sleep aids have been utilized to achieve more regular sleep cycles and induce sleep to prevent sleep deficiency or deprivation, and to treat insomnia. For example, sedatives such as zolpidem are used to treat short term sleeping problems by reducing the time to sleep onset. Although zolpidem is highly effective at inducing sleep, it has numerous adverse effects the following day such as drowsiness, headache, dizziness, and gastrointestinal distress. These symptoms are often compared to a "hangover." Zolpidem also has been associated with drug tolerance, dependence, and withdrawal, and has risks of overdose.

Another sleep aid that is often used over-the-counter is the dietary supplement melatonin, a naturally-occurring hormone produced by the pineal gland in the brain. Melatonin plays a critical role in the body's natural sleep-wake cycle. Melatonin is often used to provide relief from insomnia and jet lag associated with time change. Although melatonin is safe for short term use, it has negative side effects including headache, dizziness, nausea, and drowsiness. Melatonin can also have negative interactions with various medications in the long-term and is not suitable for some patients.

Another treatment for insomnia and sleeping disorders is cognitive behavioral therapy (CBT) in which patients consult with a sleep therapist to improve healthy sleeping habits. CBT often employs stimulus control therapy, such as avoiding naps and going to sleep only when one is tired, reducing the time spent in bed, avoiding caffeine late in the day, improving the sleep environment, relaxation training, and biofeedback. However, CBT may not be effective in all patients and may need to be combined with medications to become effective. CBT is also dependent on the user and takes a significant amount of effort to be successful.

A common problem with current compositions for improving sleep is that these medications have a sedative effect and cause drowsiness. Therefore, what is needed is a composition taken in the evening that supports brain pathways involved in sleep without sedating the consumer and causing an unpleasant experience the following day. This need has heretofore remained unsatisfied.

SUMMARY OF THE INVENTION

The present invention is directed to a dietary supplement designed to support the body's natural pathways in order to achieve relaxation and calmness, non-sedating readiness for sleep, restorative sleep, long term brain health and function, next day energy and mental performance, as well as supporting stem cell performance.

In one embodiment of the invention, a dietary supplement composition comprises: L-tryptophan, L-theanine, Reishi mushroom extract, uridine, grape and/or olive polyphenols, and paeoniflorin. In another embodiment of the present invention, the composition further comprises citrus bioflavonoid extract, γ-Oryzanol, Holy Basil extract (*Ocimum sanctum*), saffron extract, *Schisandra chinensis* extract, sesamin (sesame) extract, blueberry extract, quercetin, *Polygala tenuifolia* root extract, *Ziziphus* jujube extract, gotu kola extract (*Centella asiatica*), ashwagandha extract (*Withania somnifera*), betaine (trimethylglycine), magnesium, or vitamin B6, or any combination thereof. In another embodiment of the invention, the composition further comprises astaxanthin, lycopene, or hawthorn extract (*Crataegus* sp), or any combination thereof.

In an exemplary embodiment of the invention, the composition is integrated into a capsule, tablet, chewable tablet, or pill to be taken orally.

The advantages of the invention include inducing a sense of relaxation and calmness. Other advantages include improved sleep while not causing sedative or hypnotic effects. Other advantages include a more productive following day.

The foregoing, and other features and advantages of the invention, will be apparent from the following, more particular description of the preferred embodiments of the invention, and the accompanying drawings.

BRIEF DESCRIPTION OF THE DRAWINGS

For a more complete understanding of the present invention, the objects and advantages thereof, reference is now made to the ensuing descriptions taken in connection with the accompanying drawings briefly described as follows:

FIG. 1 illustrates a composition according to an embodiment of the invention;

FIG. 2 illustrates a table of exemplary amounts of ingredients, all of various subsets of which are found in one or more embodiments of the present invention; and FIG. 3 illustrates a table of exemplary amounts of ingredients, all of various subsets of which are found in one or more embodiments of the present invention.

DETAILED DESCRIPTION OF THE EMBODIMENTS

Preferred embodiments of the present invention and their advantages may be understood by referring to FIGS. 1-3. Further features and advantages of the invention, as well as the structure and operation of various embodiments of the invention, are described in detail below. Although the invention is described in the context of a compound, any form may be implemented such as, but not limited to a powder, a pill, or a liquid, or other form suitable for various administrations.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Moreover, the described features, structures, or characteristics of the invention may be combined in any suitable manner in one or more embodiments. It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents. Reference will now be made in detail to the preferred embodiments of the invention.

In an exemplary embodiment of the present invention and with reference to FIG. 1, a dietary supplement that improves sleep comprises L-Tryptophan, L-Theanine, Reishi mushroom extract (*Ganoderma lingzhi*), uridine, grape and/or olive polyphenols (fruit, vine seed), and paeoniflorin (from white peony root extract). In one embodiment of the invention, the total mg in one dose is 2745 mg and is taken in four capsules (686 mg/capsule). L-Tryptophan, an essential amino acid found in dietary sources such as poultry, is a precursor for neurotransmitters such as serotonin and melatonin, and is thought to play a critical role in stabilizing mood and regulating sleep. Tryptophan is sold over-the-counter and is frequently used as an antidepressant and as a sleep aid. L-Theanine, often referred to simply as theanine, is an amino acid analogue of L-glutamate and L-glutamine that is primarily found in plant and fungal species and is present in brewed tea. Theanine increases serotonin, dopamine, GABA, glycine, BDNF, and NGF levels in the brain. Theanine has a similar chemical structure to glutamate, the most abundant excitatory neurotransmitter in the brain. Reishi mushroom extract (*Ganoderma lingzhi*)—also known as the lingzhi mushroom—produces ganoderic acids, which are similar in chemical structure to steroid hormones. It possesses anti-inflammatory properties and improves circulation. Uridine (as Uridine-5'-monophosphoric acid disodium salt), one of the five nucleotides that is found in RNA, but not DNA is thought to increase RNA levels, including in the brain, leading to better cognitive function. Polyphenols (fruit, vine, seed) are organic chemicals composed of multiple sets of phenol structural units that are present in olives and grapes. Polyphenols have been suggested to have positive health effects including for cardiovascular health and as an antioxidant. Paeoniflorin (from white peony root extract) is thought to reduce neuroinflammation and has activity on adenosine receptors, which are believed to be part of the sleep-wake homeostatic system.

The present composition may be administered orally. In such an embodiment, the sleep aid may be integrated into a liquid, capsule, tablet, chewable tablet, or pill. In an exemplary embodiment, the composition is integrated into capsules and taken orally with dinner and/or in the time period leading up to bedtime (approximately 1.5-3 hours prior to desired bedtime).

The composition works unexpectedly well in that by taking the composition several hours before bedtime, the composition has a more robust effect in inducing sleep naturally. The method of taking the composition several hours before bedtime, as opposed to just prior to sleep as described in previous sleep compositions, results in a more productive day after sleep by not causing sedative-like effects. The composition further works unexpectedly well in that by combining smaller doses of compounds that assist with the brain's sleep pathways with anti-oxidant and anti-inflammatory chemical compounds, the composition assists with sleep but additionally makes the user have a more productive day the following day. The constituents form a synergistic compound where the combined effect is greater than the sum of their separate effects.

In an exemplary embodiment of the present invention and with reference to FIG. 2, the composition further comprises one or more of the following ingredients: citrus bioflavonoid extract, ©-Oryzanol, holy basil extract (*Ocimum sanctum*), saffron extract (*C rocus sativa*), *Schisandra chinensis* extract, sesamin extract, blueberry extract, quercetin, *P olygala tenuifolia* root extract, *Ziziphus jujube* extract, gotu kola extract (*Centella asiatica*), ashwagandha extract (*Withania somnifera*), betaine (trimethylglycine), magnesium, and vitamin B6. In one embodiment of the invention, the total mg in one dose is 2745 mg and is taken in four capsules (686 mg/capsule). Citrus bioflavonoid extract and other flavonoids such as naringin have shown to have strong anti-inflammatory and antioxidant activities. ©-Oryzanol is a mixture of lipids that is derived from rice bran oil and some fruits and vegetables. ©-Oryzanol contains triterpenes and sterols. ©-Oryzanol has anti-inflammatory and antioxidant properties. Holy Basil Extract 2% Ursolic Acid (*Ocimum sanctum*) is an herb that is grown throughout India and Southeast Asia. One chemical compound present in Holy Basil is ursolic acid, which has been shown to induce neural regeneration in mice. Saffron extract is an extract derived from the spice saffron, which is cultivated from the stigma of the flower *C rocus sativus*. Saffron has been used in traditional folk medicine. Saffron has small levels of vitamins B and C and contains minerals including copper, iron, magnesium, phosphorus, and potassium. Saffron contains a higher percentage of the mineral manganese. *Schisandra chinensis* extract 9% Schisandrins, also referred to as *magnolia*-vine, Chinese *magnolia*-vine, and *Schisandra*, is a wooded vine plant native to China that bears fruit called *magnolia* berry or five-flavor-fruit. *Schisandra chinensis* has been shown to have anti-inflammatory properties and has been used in traditional Chinese medicine. Sesame extract (10% sesamin) is derived from a flowering plant known for its culinary uses of sesame seeds. Sesame seeds contain high levels of vitamins and minerals, including magnesium, as well as sesamin, a lignan or polyphenol that has been suggested to possibly reduce dietary fat and act as an anti-inflammatory and antioxidant. Wild Blueberry Extract (Blueberry, Wild, Freeze Dried Powder, 1.5% Anthocyanins N11), including but not limited to, ThinkBlue™, contains flavonoids, a type of polyphenol, and is an antioxidant. Studies have shown that foods rich in flavonoids may have a positive effect on mood. Quercetin (as Quercetin dihydrate) is a flavonoid present in fruits, vegetables, and grains. Quercetin has antioxidant and anti-inflammatory properties and has been hypothesized to improve mental performance. *Polygala tenuifolia* Root Extract (10:1) is an herb native to Asia. *Polygala tenuifolia* has been shown to induce sleep to a similar efficacy as alprazolam, a manufactured benzodiazepine drug that is used to relieve anxiety. *Ziziphus jujuba* (Wild Jujube Seed Extract 2% Total Saponins), often referred to as jujube, red date, or Chinese date, is a fruiting shrub that has been used in traditional Chinese and Korean medicine to treat anxiety. Gotu Kola Extract (*Centella asiatica*) 10% Asiaticosides is an herbaceous plant that primarily grows in Asia. Gotu Kola, also known as Indian pennywort, Asiatic pennywort, or Mandookparni, has been used for medicinal purposes to treat various disorders. *Withania somnifera* extract is a plant within the nightshade family of the ashwagandha plant. *Withania somnifera*, also referred to as ashwagandha, has been used in traditional Indian medicine and is thought to help relieve stress and anxiety. Betaine anhydrous (trimethylglycine), often simply referred to as betaine, is an amino acid derivative that is found in numerous plants including sugar beets, spinach, and whole grains. Betaine is important for the metabolism of homocysteine, an amino acid found in the blood. Excess homocysteine has been shown to be related to cardiovascular disease. Magnesium (as magnesium glycinate) is an essential mineral that is critical for every day well-being. Some evidence has shown that magnesium can have a positive effect on sleep. However, too much magnesium can cause gastrointestinal discomfort and can interact with certain medications. Vitamin B6 (as pyridoxal 5'-phosphate) is an essential vitamin that is part of the vitamin B group of essential nutrients. Vitamin B6 is important for neurotransmitter synthesis.

In an exemplary embodiment of the present invention and with reference to FIG. 3, the composition further comprises astaxanthin, lycopene, and hawthorn extract (C rataegus sp). In one embodiment of the invention, the total mg in one dose is 2745 mg and is taken in four capsules (686 mg/capsule). Astaxanthin is a keto-carotenoid and is classified as a terpene. Astaxanthin is used as a dietary supplement and is thought to have antioxidant and anti-inflammatory properties. Lycopene is a carotenoid hydrocarbon that is commonly found in tomatoes and carrots and other red fruits and vegetables. Some research has shown that lycopene may have a positive effect on cardiovascular health and support GABA, an inhibitory neurotransmitter, levels in the brain. Hawthorn extract (*crataegus* sp) is a plant whose leaves, berries, and flowers may have positive effects on cardiovascular health. VINEATROL®20 grapevine extract is an extract from grapevine shoots from *Vitis vinifera*. Vineatrol® is rich in resveratrol, a phenol present in the skin of grapes. Resveratrol has been hypothesized to improve lifespan and have positive effects on cardiovascular disease, cancer, memory, and metabolism. Resveratrol has been shown to increase cell viability and enhance the functionality of mesenchymal stem cells, which eventually propagate to become neurons amongst other cell types.

In addition to the exemplary ingredients disclosed, other ingredients may be used to assist administration. In an example where the sleep aid is integrated into a capsule or tablet, the composition may also include binding agents or other inactive ingredients.

The present composition may be administered orally. In such an embodiment, the sleep aid may be integrated into a liquid, capsule, tablet, chewable tablet, or pill. In an exemplary embodiment, the composition is integrated into capsules and taken orally with dinner and/or in the time period leading up to bedtime (approximately 1.5-3 hours prior to desired bedtime). In such an embodiment, a dietary supplement to improve sleep may be prepared by first combining L-Tryptophan, L-Theanine, Reishi mushroom extract, uridine, polyphenols, and paeoniflorin (as exemplary ingredients) and mixing until a homogeneous mixture is produced. The composition may then be integrated into capsules to be taken orally.

The present disclosure may also be administered to a patient in other ways without departing from the embodiments contemplated herein including: pressing into a tablet form, including in a food or beverage, and other related methods of oral ingestion.

To make the composition, one takes the ingredients as described in the exemplary embodiments and mixes them in powder form until a homogeneous mixture is achieved. The composition is then packaged into capsules to be taken orally.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A method for promoting the brain pathways involved in sleep, relaxation, and calmness comprising:
    ingesting a composition comprising effective amounts of L-Tryptophan, L-Theanine, Reishi mushroom extract, Uridine, a polyphenol, and paeoniflorin to a subject in need thereof, wherein the step of ingesting occurs at least one and a half hours before bedtime.

2. The method of claim 1, wherein the composition further comprises citrus bioflavonoid extract, γ-Oryzanol, holy basil extract, saffron extract, *Schisandra chinensis* extract, sesamin extract, blueberry extract, quercetin, *Polygala tenuifolia* root extract, gotu kola extract, ashwagandha extract, betaine, magnesium, or combinations thereof.

3. The method of claim 1, wherein the composition further comprises astaxanthin, lycopene, hawthorn extract, or combinations thereof.

4. The method of claim 1, wherein the composition is integrated into a capsule, tablet, chewable tablet, or pill.

5. The method of claim 1, wherein the composition is integrated into a liquid or powder.

* * * * *